United States Patent [19]

Diggens

[11] 4,131,428
[45] Dec. 26, 1978

[54] METHOD OF ADJUSTING PH

[75] Inventor: Albert A. Diggens, Newton, Mass.

[73] Assignee: Orion Research Incorporated, Cambridge, Mass.

[21] Appl. No.: 869,316

[22] Filed: Jan. 13, 1978

Related U.S. Application Data

[63] Continuation-in-part of Ser. No. 775,210, Mar. 7, 1977, abandoned.

[51] Int. Cl.² .................... G01N 27/10; G01N 27/40; G01N 27/46
[52] U.S. Cl. .................................. 23/230 R; 204/1 T
[58] Field of Search ...................... 23/230 R; 204/1 T

[56] References Cited

U.S. PATENT DOCUMENTS

| | | | |
|---|---|---|---|
| 3,495,943 | 2/1970 | Kapff | 23/230 R |
| 3,689,222 | 9/1972 | McFarland et al. | 23/230 R |
| 3,864,087 | 2/1975 | Hirshfeld | 23/230 R X |
| 3,996,123 | 12/1976 | Kruishoop | 204/1 T |
| 4,025,308 | 5/1977 | Holman | 23/230 R |

Primary Examiner—Morris O. Wolk
Assistant Examiner—Michael S. Marcus
Attorney, Agent, or Firm—Robert W. Hagopian; John B. Miller

[57] ABSTRACT

In a potentiometric system for measuring low levels of ion activity, a method of adjusting the pH in a sample stream by the passive addition of low molecular weight acid or base reagent, without dilution of the sample stream, and without introduction of any interfering, reactive or test ions into the sample stream. A membrane is provided, permeable to the acid or base reagent used to adjust sample stream pH, and impermeable to ionic species. The membrane is placed between a reagent reservoir and the sample stream. Constant flow of the sample stream by the membrane maintains the reagent partial pressure differential between the reservoir and the stream, causing diffusion of reagent through the membrane into said stream.

26 Claims, 1 Drawing Figure

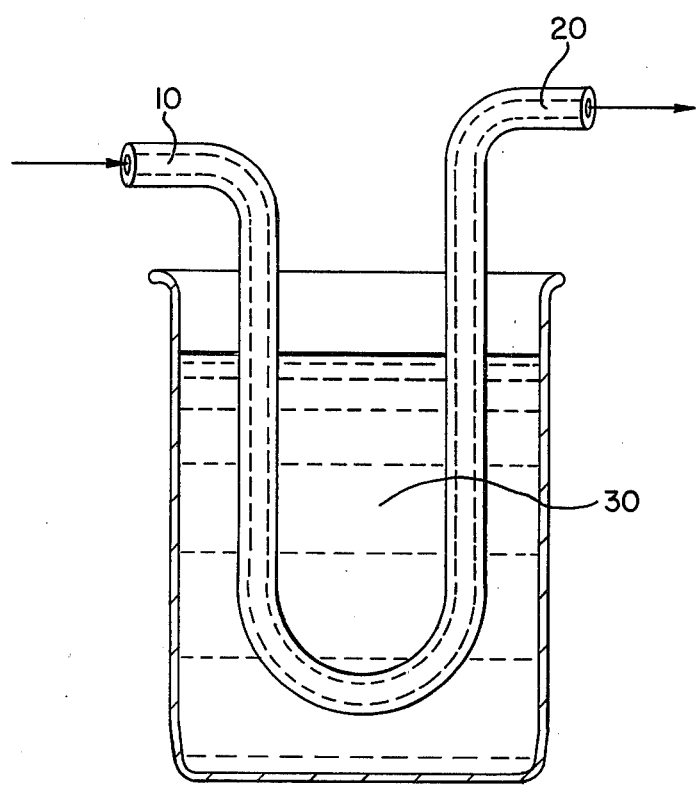

METHOD OF ADJUSTING PH

This is a continuation-in-part of application Ser. No. 775,210 filed Mar. 7, 1977 and now abandoned.

BACKGROUND OF THE INVENTION

1. Field of Invention

This invention relates to potentiometric measurements.

2. Prior Art Statement

The potentiometric determination of low levels of ion activity in a sample stream is limited by interference with electrode response caused by $H^+$ and $OH^-$ ions. If high activities of ions are being measured, the interference of $H^+$ and $OH^-$ ions is masked. At low activities, interference introduces substantial errors in measurement. Since $H^+$ and $OH^-$ are universally present in aqueous sample streams, pH adjustment prior to electrochemical testing of low level cation and anion activities is essential to accurate determinations. More specifically, addition of acid lowers pH and removes $OH^-$ from the sample stream. Addition of base raises pH and removes $H^+$ from the sample stream.

The prior art teaches that interference can be reduced by adjustment of pH. Changes in pH were made by the addition of acids or bases to the sample stream prior to electrochemical testing. The significant limitations of this method are related to the resulting dilution of the sample stream. For example, volumes added to the sample stream must be precisely metered in order to calculate original concentrations. Mixing of the sample stream and reagent must be complete, making mixing apparatus a must and creating time delays in potentiometric measurements. Real time monitoring of ionic concentrations is unattainable. For low level measurements of ion activities, dilution with a reagent may introduce an unknown amount of interfering, reactive, or even test ions in concentrations comparable to those in the sample stream.

An improved technique of pH adjustment involves the bubbling of an alkaline gas into the sample stream, thereby raising the pH. An instrument incorporating this technique is commercially available from Leeds and Northrup Company. Diethylamine gas is bubbled at a constant rate into the sample stream in an absorber column, raising pH above 11 prior to an electrochemical determination of sodium activity. Notwithstanding that pumping is still necessary to ensure that the desired volumes of gas and sample stream are contacted, the Leeds and Northrup apparatus is an advance over the solution mixing method as it dispenses with the attendant problems of sample stream dilution.

The chief disadvantage of the apparatus is that contaminants are bubbled into the stream. Additionally, the absorber column is bulky and creates a delay in measurement, reducing the system's ability to monitor in real time.

SUMMARY OF INVENTION

The present invention contemplates a new method of adjusting the pH of a sample stream in a potentiometric system for measuring low levels of ion activity.

One object of the invention is to provide a method of adjusting the pH of the sample stream by the addition of acid or base reagent without introducing any interfering or reactive ions into the stream.

Another object of the invention is to adjust the pH of the sample stream by the passive addition of reagent. By passive, it is meant that reagent is added using the partial pressure difference between the reagent and the sample stream as the driving diffusion mechanism, dispensing with the need for metering, mixing machinery and pumps.

Another object is to provide a method of adjusting the pH of the sample stream without diluting the stream.

The objects of the present invention are attained by providing a membrane, permeable to the acid or base reagent used to adjust sample stream pH, and impermeable to ionic species. The acid or base reagent, being neutrally-charged, passes through the membrane without difficulty. The membrane is placed between a reservoir of the reagent and the sample stream. The flow of the sample stream past the membrane causes the diffusion of reagent through the membrane into said stream, thereby adjusting the pH of the stream.

These and other objects, aspects and advantages of the present invention will become more apparent with the following specification and the scope of the application of which will be indicated in the claims.

BRIEF DESCRIPTION OF THE DRAWINGS

The drawing shows a diagrammatic, side elevational, cross-sectional view of a preferred form of the present invention.

PREFERRED EMBODIMENTS

Referring now to the drawing, there is shown a preferred form of the present invention. Hollow membrane tube 20 carries sample stream 10. The tube is immersed in reagent reservoir 30, containing the acid or base to be added to the sample stream 10. The tube is composed of a material permeable to the reagent used to adjust sample stream pH and impermeable to ionic species. Typical examples are silicone rubber, silicone polycarbonate copolymer, microporous teflon, and microporous polypropylene. Diffusion of neutrally charged acid or base occurs from the reagent reservoir 30 through the membrane tube 20 into the sample stream 10. This is due to the difference in the partial pressures of the acid or base in reservoir 30 and stream 10. While diffusion of sample stream through the membrane tube into the reservoir also occur, ionic species cannot move through the membrane tube. Thus, ionic concentrations are not affected by the diffusion process. Reagent is added passively in the sense that it is the partial pressure difference between the reagent and the sample stream that is the driving mechanism behind the diffusion of reagent across the membrane. The use of metering, mixing and pumping machinery is not required.

The selection of a suitable membrane tube material depends on the corrosive nature of the reagent, the wetting characteristics of the membrane, and the rate of reagent diffusion required to adjust pH in the specified design time.

Ideally, the membrane is made from an inert, large pore volume material possessing permanent non-wetting characteristics. It is obviously desirable that the membrane be unchanged by either the reagent or the sample stream. A large pore volume material will permit rapid reagent transport. If the membrane is wetted (i.e., allows liquid transport through the material), the liquid transport into the sample stream will dilute the stream, there frustrating the objects of the invention.

It may be necessary to compromise this ideal. For example, the microporous (large pore volume) membranes are superior to silicone rubber membranes when it comes to reagent transport; but, since they will eventually become wetted, they enjoy a shorter service life.

Membrane degradation problems may be solved by (1) selecting a more inert membrane material, or (2) suspending the tube 20 in the vapor space above the reagent reservoir 30. This vapor space acts as an additional ion-permeable membrane, and reduces the membrane corrosion rate.

The rate of reagent diffusion required to adjust pH in a specified design time is a function of the flux of reagent 30 through the tube 20. The flux of any particular reagent, in moles/unit of tube surface/unit time, is described by equation 1, where F is the flux, $C_{mem}$ is the concentration (or pressure) differential across the membrane, D is the diffusion coefficient of the membrane, and W is the width of the membrane.

$$F = (C_{mem})(D)/W \qquad (1)$$

$C_{mem}$ is related to $C_{aq}$, the concentration (or pressure) differential between the reservoir and the sample stream according to equation (2), where 1/K is the solubility coefficient.

$$C_{mem} = C_{aq}(1/K) \qquad (2)$$

The permeability of the membrane, P, is the product of the diffusion coefficient and the solubility coefficient. The flux is then described by equation 3.

$$F = (C_{aq})(P)/W \qquad (3)$$

As equation (3) shows, the flux is controlled by the geometry of the tubing, the permeability of the tubing, and the concentration (or pressure) differential between the reagent 30 and the sample stream 20.

Low molecular weight reagents, all else being equal, diffuse more quickly than high molecular weight reagents, and are therefore preferred. Suitable low molecular weight acid reagents include acetic acid, propionic acid, formic acid, hydrogen iodide, and hydrochloric acid. Suitable low molecular weight base reagents include ammonium hydroxide, piperidine, and dimethylamine.

The membrane material is selected to optimize the above factors: reagent corrosion, material wetting properties, useful life, tube geometry, material permeability, and concentration (or pressure) differential. Typical tube materials are silicone rubber (available as Ja-Bar Formulation 5509 from Ja-Bar, Inc., Andover, Maryland), silicone polycarbonate copolymer (available as MEM213 from the General Electric Company, Schenectady, N.Y.), microporous teflon (available as Gore-Tex from W. L. Gore & Associates, Inc., Elkton, Md.), and microporous polypropylene (available as Celgard® 2400 from the Celanese Plastics Company, Newark, N.J.). The selected material should provide the optimum rate of reagent diffusion over the design life.

Following are two descriptive examples of the use of the invention. Quantitative data on these and other examples are contained in Table 1 below.

EXAMPLE I

The potentiometric measurement of sodium ion activities on the order of $10^{-7}$ in a high purity water stream is difficult if the pH is less than ten. At a pH of less than 10, there are enough hydrogen ions present to substantially interfere with electrochemical monitoring techniques. For the potentiometric measurement of low $Na^+$ activities to be successful, the pH of the water stream must be adjusted too a value greater than ten. pH adjustment by mixing the water stream with an alkaline solution is inadequate for several reasons. The solution mixing method dilutes with water stream and requires precise metering of liquid volumes if activity prior to mixing is to be calculated. The mixing of the water stream with the alkaline solution also requires the use of machinery and/or pumps. When very small activities of sodium ion are to be measured, the alkaline solution is likely to have an equal or greater activity of $Na^+$ than the high purity water stream itself, introducing substantial errors in measurement.

With ammonia as the base reagent 30, the present invention passively adjusts the pH to the desired value without dilution of the water stream 10 and without introducing any interfering, reactive, or test ions into said stream. The composition of the tube 20 is silicone rubber of known permeability. The geometry of the tube and the concentration differential of ammonia between the reagent and water stream are adjusted to ensure that enough ammonia is diffused through the silicon rubber tube to raise pH over 10. The potentiometric measurement for $Na^+$ is then made using a $Na^+$ electrode and a reference electrode, without interference from $H^+$.

EXAMPLE II

The potentiometric measurement of low levels of chloride ion activity in a sample stream is difficult if the pH is greater than five. When the pH is greater than five, there are enough hydroxide ions present to substantially interfere with electrochemical monitoring techniques. For the potentiometric measurement of low $Cl^-$ activities to be successful, the pH of the sample stream must be adjusted to a value less than five. For the reasons stated in Example 1, pH adjustment by mixing the sample stream with an acid solution is wholly inadequate.

With acetic acid as the agent reagent 30, the present invention passively adjusts the pH to the desired value without dilution of the sample stream 10 and without introducing any interfering, reactive, or test ions into said stream. The composition of the tube 20 is silicone rubber of known permeability. The geometry of the tube and the concentration differential of acetic acid between the reagent and sample stream are adjusted to ensure that enough acetic acid is diffused through the silicone rubber tube to lower pH below five. The potentiometric measurement for $Cl^-$ is then made, using a $Cl^-$ electrode and a reference electrode, without interference from $OH^-$.

TABLE I

| Membrane | Reagent | Concentration | Sample pH In | Sample pH Out |
|---|---|---|---|---|
| Silicone Rubber (30" long, inside diameter ⅛", wall thickness ⅛") | Ammonia (Solution) | 27% W/V | 2.0 | 10.5 |
| | Piperidine | 25% W/V | 2.0 | 11.4 |
| | Dimethylamine | 25% W/V | 2.0 | 11.0 |
| | Acetic Acid | 100% W/V | 10.0 | 3.5 |
| | Proprionic Acid | 100% W/V | 10.0 | 3.5 |

TABLE I-continued

| Membrane | Reagent | Concentration | Sample pH In | Sample pH Out |
|---|---|---|---|---|
| Microporous Teflon (5" long, inside diameter ¼", wall thickness ⅛") | Ammonia (Solution) | 27% W/V | 2.0 | 10.5 |
| | Piperidine | 25% W/V | 2.0 | 11.4 |
| | Dimethylamine | 25% W/V | 2.0 | 11.0 |
| | Acetic Acid | 100% W/V | 10.0 | 3.5 |
| | Proprionic Acid | 100% W/V | 10.0 | 3.5 |
| | Hydrochloric Acid | 37% W/V | 13.0 | 2.0 |
| Microporous Polypropylene (5" long, inside diameter ¼", wall thickness ⅛") | Ammonia (Solution) | 27% W/V | 2.0 | 10.0 |
| | Piperidine | 25% W/V | 2.0 | 10.0 |
| | Dimethylamine | 25% W/V | 2.0 | 10.0 |
| | Acetic Acid | 100% W/V | 10.0 | 3.5 |
| | Proprionic Acid | 100% W/V | 10.0 | 3.5 |
| | Hydrochloric Acid | 37% W/V | 13.0 | 2.0 |

Silicone Polycarbonate Copolymer (MEM-213) from the General Electric Company, Schenectady, N.Y.) is available in sheets. By using sheets of this material to separate the reagent from the sample stream pH can be adjusted in the sample stream by diffusion of reagent. Other geometrical arrangements of the elements are non-distinct from the principles of the invention and intended to be included herein.

Since various changes may be made in the above description without departing from the scope of the present invention, it is intended that all matter contained in the above description or shown in the accompanying drawing shall be interpreted in an illustrative and not in a limiting sense.

We claim:

1. In a method for potentiometrically determining low levels of ion activity in sample streams without interference of hydrogen ion, the improvement comprising:
    continuously passing the sample stream over one side of an inert non-impermeable non-wetting membrane that is permeable to a low molecular weight base reagent; and
    diffusing a low molecular weight base reagent through the membrane and into the stream by contacting the other side of said membrane with the base reagent to thereby raise the pH of the stream to a value which eliminates interference of hydrogen ions without dilution of the sample stream and without introducing any interfering, reactive, or test ions into the sample stream.

2. The method of claim 1 further comprising:
    measuring low levels of ion activity in the sample stream.

3. The method of claim 1 wherein the base reagent is ammonia.

4. The method of claim 1 wherein the base reagent is piperidine.

5. The method of claim 1 wherein the base reagent is dimethylamine.

6. The method of claim 1 wherein the membrane is composed of silicone rubber.

7. The method of claim 1 wherein the membrane is composed of silicone polycarbonate copolymer.

8. The method of claim 1 wherein the membrane is composed of microporous teflon.

9. The method of claim 1 wherein the membrane is composed of microporous polypropylene.

10. In a method for potentiometrically determining low levels of ion activity in sample streams without interference of hydroxyl ion, the improvement comprising:
    continuously passing the sample stream over one side of an inert non-impermeable non-wetting membrane that is permeable to a low molecular weight acid reagent; and
    diffusing a low molecular weight acid reagent through the membrane and into the stream by contacting the other side of said membrane with the acid reagent to thereby lower the pH of the stream to a value which eliminates interference of hydroxyl ions without dilution of the sample stream and without introducing any interfering, reactive, or test ions into the sample stream.

11. The method of claim 10 further comprising:
    measuring low levels of ion activity in the sample stream.

12. The method of claim 10 wherein the acid reagent is acetic acid.

13. The method of claim 10 wherein the acid reagent is propionic acid.

14. The method of claim 10 wherein the acid reagent is hydrochloric acid.

15. The method of claim 10 wherein the acid reagent is hydrogen iodide, HI.

16. The method of claim 10 wherein the acid reagent is formic acid, $CH_2O_2$.

17. The method of claim 10 wherein the membrane is composed of silicone rubber.

18. The method of claim 10 wherein the membrane is composed of silicone polycarbonate copolymer.

19. The method of claim 10 wherein the membrane is composed of microporous teflon.

20. The method of claim 10 wherein the membrane is composed of microporous polypropylene.

21. In a method for potentiometrically determining low levels of sodium ion activity in sample streams without interference of hydrogen ion, the improvement comprising:
    continuously passing the sample stream over one side of an inert ion-impermeable non-wetting membrane that is permeable to piperidine; and
    diffusing piperidine through the membrane and into the stream by contacting the other side of said membrane with the piperidine to thereby raise the pH of the stream to a value which eliminates interference of hydrogen ions without dilution of the sample stream and without introducing any interfering, reactive, or test ions into the sample stream.

22. In a method for potentiometrically determining low levels of chloride ion activity in sample streams without interference of hydroxyl ion, the improvement comprising:
    continuously passing the sample stream over one side of an inert non-impermeable non-wetting membrane that is permeable to acetic acid; and
    diffusing acetic acid through the membrane and into the stream by contacting the other side of said membrane with the acetic acid to thereby lower the pH of the stream to a value which eliminates interference of hydroxyl ions without dilution of the sample stream and without introducing any interfering, reactive, or test ions into the sample stream.

23. In a method for potentiometrically determining low levels of ion activity in sample streams without interference of hydrogen ion, the improvement comprising:
continuously passing the sample stream over one side of an inert ion-impermeable non-wetting membrane that is permeable to ammonia; and
diffusing ammonia through the membrane and into the stream by contacting the other side of said membrane with the ammonia to thereby raise the pH of the stream to a value which eliminates interference of hydrogen ions without dilution of the sample stream and without introducing any interfering, reactive, or test ions into the sample stream.

24. In a method for potentionmetrically determining low levels of sodium ion activity in high purity water streams without interference of hydrogen ion, the improvement comprising:
continuously passing the sample stream over one side of an inert ion-impermeable non-wetting membrane that is permeable to a low molecular weight base reagent; and
diffusing a low molecular weight base reagent through the membrane and into the stream by contacting the other side of said membrane with the base reagent to thereby raise the pH of the stream to a value which eliminates interference of hydrogen ions without dilution of the sample stream and without introducing any interfering, reactive, or test ions into the sample stream.

25. The method of claim 24 wherein the base reagent is ammonia.

26. The method of claim 24 wherein the base reagent is piperidine.

* * * * *